US012765801B2

(12) United States Patent
Mikaelian

(10) Patent No.: US 12,765,801 B2
(45) Date of Patent: Oct. 20, 2026

(54) INTEGRATED SAMPLING AND ANALYSIS DEVICE

(71) Applicant: miDiagnostics NV, Heverlee (BE)

(72) Inventor: David Mikaelian, Brussels (BE)

(73) Assignee: MIDIAGNOSTICS NV, Leuven (BE)

( * ) Notice: Subject to any disclaimer, the term of this patent is extended or adjusted under 35 U.S.C. 154(b) by 731 days.

(21) Appl. No.: 18/136,635

(22) Filed: Apr. 19, 2023

(65) Prior Publication Data

US 2023/0337939 A1 Oct. 26, 2023

(30) Foreign Application Priority Data

Apr. 20, 2022 (EP) .................................... 22169126

(51) Int. Cl.

| | |
|---|---|
| ***A61B 5/097*** | (2006.01) |
| ***A61B 5/08*** | (2006.01) |
| ***G01N 33/00*** | (2006.01) |
| ***G01N 33/497*** | (2006.01) |
| ***G01N 33/569*** | (2006.01) |

(52) U.S. Cl.

CPC .............. *A61B 5/097* (2013.01); *A61B 5/082* (2013.01); *G01N 33/0031* (2013.01); *G01N 33/497* (2013.01); *A61B 2560/0406* (2013.01); *A61B 2562/0247* (2013.01); *A61B 2562/0271* (2013.01); *A61B 2562/029* (2013.01); *G01N 33/56983* (2013.01); *G01N 2800/00* (2013.01)

(58) Field of Classification Search

CPC . A61B 5/097; A61B 5/082; A61B 2560/0406; A61B 2562/0247; A61B 2562/0271; A61B 2562/029; A61B 5/087; G01N 33/0031; G01N 33/497; G01N 33/56983; G01N 2800/00

See application file for complete search history.

(56) References Cited

U.S. PATENT DOCUMENTS 5,039,490 A * 8/1991 Marsoner ............. G01N 21/255 356/402
2004/0097820 A1* 5/2004 Bradley ................. A61B 5/087 600/529
2008/0038207 A1* 2/2008 Edwards .............. G01N 33/497 424/44

(Continued)

FOREIGN PATENT DOCUMENTS

WO WO2018/126119 A1 7/2018

OTHER PUBLICATIONS

European Search Report from corresponding European Patent Application No. 22169126, dated Sep. 1, 2022.

*Primary Examiner* — Adam J Eiseman
*Assistant Examiner* — Lucy Eppert
(74) *Attorney, Agent, or Firm* — RENNER, OTTO, BOISSELLE & SKLAR, LLP

(57) ABSTRACT

The field of the invention generally relates to sample collection, for example of a sample being an exhaled breath. In particular, an integrated device is disclosed herein comprising a silicon chip for sampling particulate matter from a sample and for analysis, preferably by a protocol using thermocycling, of the particulate matter as collected from the sample. Further, point-of-care (PoC) and self-use analysis systems compatible with the integrated device, and methods related to sample collection and/or analysis using the same, are also disclosed.

28 Claims, 8 Drawing Sheets

(56) References Cited

U.S. PATENT DOCUMENTS

| | | | | |
|---|---|---|---|---|
| 2013/0209991 | A1* | 8/2013 | Wang | A61B 5/1473 435/7.1 |
| 2015/0038356 | A1* | 2/2015 | Karlin-Neumann | C12Q 1/6827 435/5 |
| 2015/0105683 | A1* | 4/2015 | Bos | A61B 5/7405 600/532 |
| 2017/0128008 | A1* | 5/2017 | Chung | A61B 5/15 |
| 2017/0164906 | A1* | 6/2017 | Ramanan | A61B 5/087 |
| 2020/0221973 | A1 | 7/2020 | Hojer | |
| 2020/0245898 | A1 | 8/2020 | Heanue et al. | |
| 2022/0192535 | A1* | 6/2022 | Atsalakis | A61B 5/097 |
| 2023/0010415 | A1* | 1/2023 | Christopher | A61B 5/031 |
| 2024/0260859 | A1* | 8/2024 | Amatore | A61B 10/0064 |
| 2024/0335137 | A1* | 10/2024 | Hannis | A61B 5/082 |

* cited by examiner

INTEGRATED SAMPLING AND ANALYSIS DEVICE

TECHNICAL FIELD

The field of the invention generally relates to sample collection, for example of a sample being an exhaled breath. In particular, an integrated device is disclosed herein comprising a silicon chip for sampling particulate matter from a sample and for analysis, preferably by a protocol using thermocycling, of the particulate matter as collected from the sample. Further, point-of-care (PoC) and self-use analysis systems compatible with the integrated device, and methods related to sample collection and/or analysis using the same, are also disclosed.

BACKGROUND

Infection control and prevention depends on disrupting the transmission of pathogens from the infected animal or human to new hosts or locations.

Rapid screening and low-cost diagnosis play a crucial role in choosing the correct course of intervention and in controlling disease outbreaks. This is especially important if the disease-causing agent has no effective treatment.

The transmission of microorganisms can be divided into five main routes: direct contact, fomites, aerosol (airborne), oral (ingestion), and vectorborne. Some disease-causing agents can be transmitted by more than one route. Respiratory viruses such as influenza and corona viruses, are believed to be spread from the respiratory tract mainly through breathing and coughing. Spread can be mitigated by measures such as applying basic hygiene rules, maintaining safe distances from others, preventing close person-to-person contact with infected individuals, along with a rapid detection of infections.

Traditional approaches for testing respiratory infections use throat swab samples, nasal swab samples and nasopharyngeal swab samples. Swab insertion and removal can be uncomfortable, especially for children, and may be risky for patients with sinus pathology.

Less intrusive sampling methods that are easier to implement and compact integrated solutions for the rapid testing of infectious diseases without loss of sensitivity are thus desired.

SUMMARY

There is robust evidence supporting airborne transmission of many respiratory viruses. Consequently, one object of the present disclosure is to overcome the limitations of the currently existing sampling techniques and tools used to, for example, detect respiratory tract infections.

A further object of the present disclosure is to overcome the limitations of current biosensor-based detection techniques.

A yet another object of the disclose is to provide a fast method from sampling to accurate detection for the early diagnosis of respiratory tract infections and to provide systems useful therefor.

These and other objects will be evident to the skilled person from the teachings as explained herein, and are met by different aspects of the disclosure that follows below and in the appended claims.

In line with the above, according to a first and very general aspect, a collecting device (1) is hereby provided for sampling particulate matter from a sample, the sample for example being breath exhaled by a user, the collecting device comprising a base structure (10), a monolithic silicon chip (2) supported by said base structure (10), the chip (2) comprising at least two opposite sides and a top surface (2T) and an opposite thereto bottom surface (2B), wherein the bottom surface (2B) is closed allowing contacting with a heating source and wherein the top surface (2T) comprises a plurality of patterned impaction channels (21) for capturing particulate matter present in the sample, for example the exhaled breath, and extending between the at least two opposite sides of the chip, each one of the impaction channels (21) comprising at least one impaction channel inlet (212) and at least one impaction channel outlet (213) and comprising one or more T-junctions (211) between the at least one impaction channel inlet (212) and the at least one impaction channel outlet (213);

the collecting device further comprising a cover (3) in contact with the base structure (10) and comprising a chip-contacting layer (30) that is in contact with the chip's top surface (2T) and is at least partially covering the impaction channels (21), wherein the cover (3) is configured to define at least one sample inlet opening (32) and at least one sample outlet opening (33), and further to define together with the chip's top (2T) surface an at least one sample inlet channel (22, 322) that is in fluidic connection with the at least one impaction channel inlet (212) and that is arranged for guiding at least a part of the sample into the one or more T-junctions, and an at least one sample outlet channel (23, 323) that is in fluidic connection with the at least one impaction channel outlet (213) and that is positioned downstream of the one or more T-junctions, wherein the cover (3) is arranged such that fluidic connection between the at least one sample inlet channel (22, 322) and the at least one sample outlet channel (23, 323) is established by the one or more one or more of T-junctions (211), and wherein the collecting device (1) further comprises a transparent zone (3211) that covers an area of the top surface (2T) of the chip (2), which area comprises the one or more of T-junctions (211) for presenting said area to light-based detection of an analyte possibly captured in said one or more of T-junctions (211).

In a particularly advantageous aspect, an embodiment of the collecting device (1) is provided wherein at least one of the layers of the cover (3) comprises one or more openings comprising at least a first opening corresponding to the at least one sample inlet opening (32), and possibly further comprises a second opening corresponding to the at least one sample outlet opening (33), possibly wherein the at least one of the layers of the cover (3) is the chip-contacting layer (30).

In a further aspect, a breath analyser comprising the collecting device (1) is provided, the breath analyser also comprising a mouthpiece wherein the cross-section of the part of the mouthpiece designed to engage with the user's lips is defined by two wider rims and two perpendicular thereto shorter rims defining the positioning of the mouthpiece with respect to the lips of the user, wherein the collecting device (1) is positioned such that the chip (2) is positioned horizontally with respect to the wider rims of the mouthpiece such that the chip (2) is positioned horizontally with respect to the ground level and/or to the base structure (10) and to the flow of air that the user exhales into the card/collecting device via the mouthpiece.

In an embodiment, the breath analyser as disclosed herein uses horizontal positioning of the chip (2) with respect to the flow of the air that the user exhales during breath sample collection. For example, if the air is exhaled by the user and enters into the collecting device (1) horizontally with respect to the ground level, the chip (2) will be positioned horizontally with respect to the ground level too. This means that during such breath collecting process, while the user exhales, the chip's major plane is laid approximately flat above the ground level which is beneficial for the particulate collection process and a direct and straightforward transferring of the collecting device (1) without agitating the chip (2) into a diagnostic system for immediate analysis.

In line with the above, in a yet further aspect, a diagnostic system is also provided herein, the diagnostic system comprising the collecting device (1) according to the present disclosure, wherein the system further comprises a heating module and a reader, and wherein the system is engageable with the collecting device (1) and adapted to perform thermocycling directly on the chip (1) followed by reading the output signals as generated during the sample analysis also directly from the chip (2).

In a yet another aspect, uses of the collecting device and/or the system of the disclosure are provided, for testing a user for a presence of a metabolic condition or a disease, the disease preferably being an infectious disease caused by an infectious agent, even more preferably being an infectious disease caused by an infectious agent that undergoes shedding into material exhaled by a user, most preferably being a virus such as SARS-CoV-2 virus.

Definitions

The disclosed products, kits, kits of parts, systems, or components, relate to a collecting device, e.g. test card for an automated system, possibly a PoC or self-use system or device.

In general, as used herein the terms "fluidic", "microfluidic", or sometimes "nanofluidic" refers to systems and arrangements dealing with the behavior, control, and manipulation of fluids that are geometrically constrained to millimeter, sub-millimeter/sub-micrometer-scale in at least one or two dimensions (e.g. width and height of a channel or groove). Such small-volume fluids are moved, mixed, separated or otherwise processed at a micro scale requiring small size and low energy consumption. Nanofluidic systems include structures such as micro pneumatic systems (pressure sources, liquid pumps, micro valves, etc.) and nanofluidic structures for the handling of micro, nano- and picoliter volumes (microfluidic grooves, microfluidic channels, etc.).

As used herein, the terms "integrated sampling and analysis device", "microfluidic collecting device", "microfluidic collection device" and sometimes "collecting device" or "collection device" are to be treated as synonyms and construed as relating to a multi-part or multi-component assembly that is made or assembled from separately manufactured parts that is formed as a single object that can be transferred or moved as one fitting inside or outside of a larger instrument adapted to and/or suitable for accepting or connecting to such "collecting device", and wherein at least one of the parts can be identified as a "chip" or a "microfluidic chip", wherein a second of the parts can be identified as a "base structure" (also referred to as "base" or "support structure" or "support", preferably being made from a rigid material) for housing or supporting said chip, and wherein as a third part the collecting device further comprises a cover, prefer preferably a multi-layer (or multilayer) cover, wherein the cover is in contact with the chip and the base structure such that together therewith is creates a path for moving and collecting particulate matter from a sample, for example a gaseous sample like a breath sample, within the structures patterned within the chip. Advantageously, a collecting device will be a nanofluidic test card (or testcard) comprising a so called nanofluidic silicon chip, also referred to as "nanofluidic processor".

As used herein, the terms "microfluidic chip", "fluidic chip", "nanofluidic chip", "nanofluidic processor", or as used mostly herein just "chip", are to be treated synonymously and in accordance with its standard meaning within the field, construed as referring to a small physical device, the device usually made of silicon frequently monolithic, which houses a patterned fluidic circuit represented as at least one groove "patterned" in the chip's body, the groove being adapted for processing a liquid. As used herein, the "chip" will be understood as also comprising grooves patterned as "impaction channels" to comprise structures like T-junctions arranged for collecting by impaction a particulate matter present in the sample.

As used herein, the term "T-junction" is to be understood as referring to a right and/or left turn at the end of a groove. Preferably, it refers to an intersection of grooves where one groove terminates as it joins a groove and makes a sharp bend. A typical three-way intersection has an intersection angle of 120°, 110°, 100° 90°, 80, 70° or 60°.

As used herein, "impaction channels" refer to channels allowing sampling of particulate matter from a sample by impaction. Such channel will typically comprise a channel inlet, channel outlet and one or more T-junctions forcing particulate matter of a sample to make a sharp bend in its original stream allowing the collection of the larger particles on the collection surface of the T-junction.

As used herein, sampling of particulate matter from a sample by "impaction" refers to the process in which particles present in the sample are removed from a stream flow by forcing the sample to make a sharp bend in the original stream path. In simplification, it can be said that particles above a certain size possess so much momentum that they cannot follow the stream and strike a collection surface in the particles' original path. The particles on the collection surface are available for later analysis of mass and composition.

As used herein the term "particulate matter" or "aerosol" refers to a mixture of solid particles and liquid droplets emitted from a source, for instance by exhalation or exhalation events such as coughing, sneezing. Such particulate matter containing microscopic solids or liquid droplets of various sizes that can be inhaled by a susceptible subject and may cause serious health problems. Droplets tiny enough (e.g. <5 μm) may stay airborne for hours and the ultimate fate of such airborn aerosols is determined by the airflows they encounter.

In line with the above, as used herein the term "groove" is to be understood as any functionally defined compartment of any geometrical shape within the chip of the nanofluidic assembly, defined by at least one wall and comprising the means necessary for performing the processing function which is attributed to this compartment, such as e.g. sample processing and/or analysis, e.g. by nucleic acid amplification e.g. by PCR. As used herein, the chips will also comprise specific structures like T-junctions formed by the grooves, which structures will serve the purpose of collection of a particulate matter from a sample by impaction, for example being collection of aerosol particles from breath exhaled by a user within the T-junctions formed by grooved patterned within the chip's "top surface".

As used herein, the term "the top surface of the chip" is to be understood as the surface of the chip patterned, etched, etc. to comprise grooves like the T-junctions. It can also be understood as the "impaction surface" or "analytical surface" of the chip.

Similarly, the term "the bottom surface of the chip" is to be understood as the closed or flat surface of the chip, which is opposite to the patterned with grooved "top surface". The bottom surface will be closed for contacting with a heating source such as thermoelectric cooler (TEC) or another Peltier device.

As used herein, the collecting device and the compatible therewith instrument can be seen as forming an at least semi-automated system or fully-automated system, or an at least semi-automated or fully-automated platform, wherein the term "semi-automated" indicates that at least a part of the protocol as performed on the collecting device was started or performed in a non-automated way by a user, e.g. at the bench-side, possibly manually, which may include addition of appropriate reagents or manipulation of the collecting device for releasing such reagents from included therein compartments, such as blisters with appropriate reagents.

As used herein, the term "sample", is to be construed broadly as any fluid, i.e. liquid or gaseous sample potentially comprising an analyte of interest that can be collected as part of a particulate matter by impaction within appropriate grooves of the chip, which fluid can be provided into the chip for being processed on said chip. Preferably, the sample will be breath exhaled by an individual. As used herein, the analyte will usually be a target nucleic acid to be detected with the help of the chip being a part of the disclosed herein microfluidic assembly. The analyte will preferably be a detectable nucleic acid, usually being a nucleic acid of a pathogen, e.g. viral DNA or RNA, but may also contain nucleic acid from the person from whom the sample was obtained such as genomic DNA, mitochondrial DNA, mRNA, rRNA, tRNA, microRNA etc.

Also, as used herein the term "nucleic acid isolation" is to be interpreted as any form of releasing nucleic acids from a biological material like the particulate matter collected by impaction on the chip, to make it available for amplification.

As used herein the term "multi-layer cover" is to be construed as a term synonymous to a term "composite cover", which both terms relate to a specific part of an advantageous embodiment of the disclosed herein collection device, which part has a composite structure, i.e. structure of assembled together at least two but likely at least three or more distinct layers.

It is also to be understood that the terminology used herein is for purpose of describing particular embodiments only and is not intended to be limiting. It must be noted that, as used in the specification and the appended claim, the articles "a", "an", "the", and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings do not exclude other elements or steps.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, the term "multiple" in "multiple . . . " or "multiple . . . " is to be understood as referring to more than one, e.g. a plurality of . . . . In the context of a . . . , the term "multiple" will usually refer to more than 1, such as, 2, 3, 4, 5, 6, 7, 8, 9, 10 or in the range of multiples of 10.

BRIEF DESCRIPTION OF DRAWINGS

For a fuller understanding, reference is made to the following detailed description taken in conjunction with the accompanying drawings in which.

DETAILED DESCRIPTION

Figure 1:
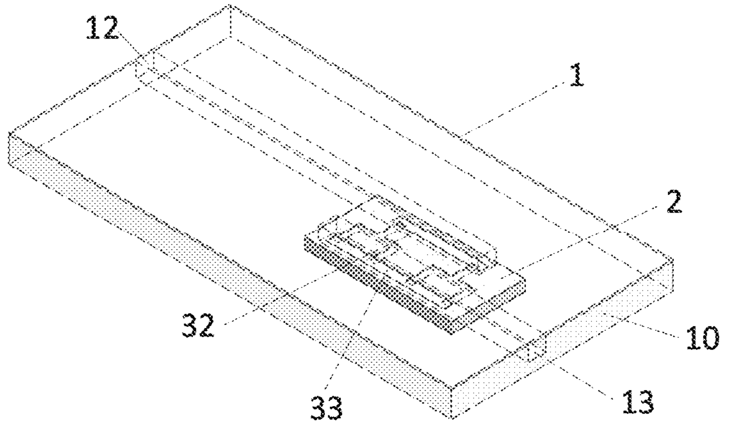
FIG. 1 schematically shows a possible embodiment of the disclosed herein collection device (1) wherein the base structure (10) comprises two sample guiding conduits (11), the first conduit (11) extending from the sample inlet (12) and positioned upstream of the chip (2) with the impaction channels, and the second conduit (11) positioned downstream of the chip (2) and leading to a sample outlet (13)

In a first general aspect, a collecting device (1) is hereby disclosed for sampling particulate matter from a sample, the sample for example being breath exhaled by a human subject, the collecting device comprising a base structure (10), a monolithic silicon chip (2) supported by said base structure (10), the chip (2) comprising at least two opposite sides and a top surface (2T) and an opposite thereto bottom surface (2B), wherein the bottom surface (2B) is closed allowing contacting with a heating source and wherein the top surface (2T) comprises a plurality of patterned impaction channels (21) for capturing particulate matter present in the sample, for example the exhaled breath, and extending between the at least two opposite sides of the chip, each one of the impaction channels (21) comprising at least one impaction channel inlet (212) and at least one impaction channel outlet (213) and comprising one or more T-junctions (211) between the at least one impaction channel inlet (212) and the at least one impaction channel outlet (213);

the collecting device further comprising a cover (3) in contact with the base structure (10) and comprising a chip-contacting layer (30) that is in contact with the chip's top surface (2T) and is at least partially covering the impaction channels (21), wherein the cover (3) is configured to define at least one sample inlet opening (32) and at least one sample outlet opening (33), and further to define together with the chip's top (2T) surface an at least one sample inlet channel (22, 322) that is in fluidic connection with the at least one impaction channel inlet (212) and that is arranged for guiding at least a part of the sample into the one or more T-junctions, and an at least one sample outlet channel (23, 323) that is in fluidic connection with the at least one impaction channel outlet (213) and that is positioned downstream of the one or more T-junctions, wherein the cover (3) is arranged such that fluidic connection between the at least one sample inlet channel (22, 322) and the at least one sample outlet channel (23, 323) is established by the one or more one or more of T-junctions (211), and wherein the collecting device (1) further comprises a transparent zone (3211) that covers, and optionally is in contact with, an area of the top surface (2T) of the chip (2), which area comprises the one or more of T-junctions (211) for presenting said area to light-based detection of an analyte possibly captured in said one or more of T-junctions (211).

In other words, an advantageously integrated sample collection and analysis device is hereby provided comprising a chip patterned with impaction channels (21) serving for both the sample collection by impaction and their subsequent analysis within the same chip's structures, wherein the above-described at least one sample inlet channel (22, 322) and the at least one sample outlet channel (23, 323) are in fluidic connection exclusively made through the one or more one or more of T-junctions (211) patterned in the chip and closed by the cover (3).

Figure 5:
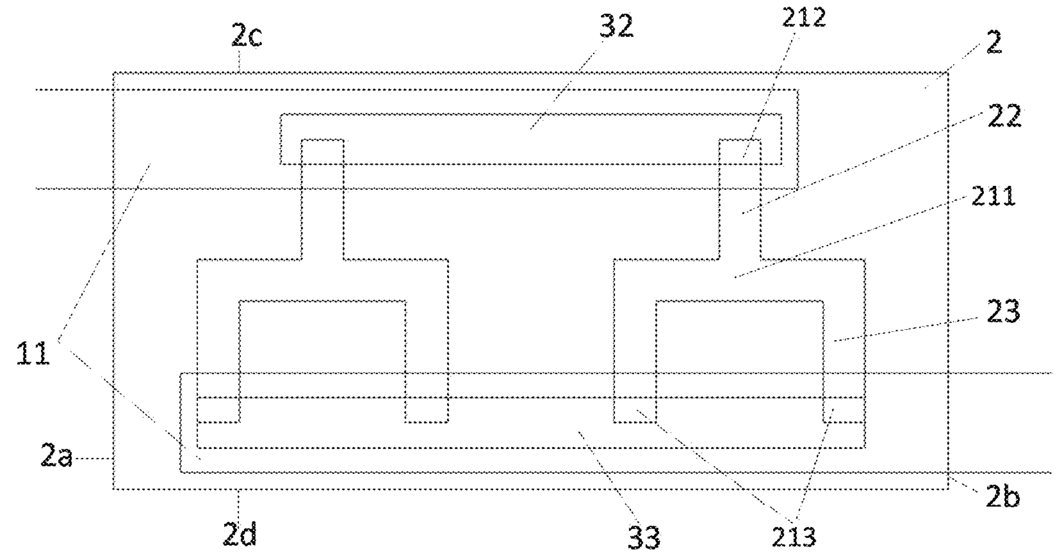
FIG. 5 shows a top-view alignment of the chip (2) and the chip-contacting layer (30) of the embodiment of the collection device from FIG. 1., which view shows that fluidic connection between the sample inlet opening (32) and the sample outlet opening (33) is made through T-junctions (211)
Figure 6:
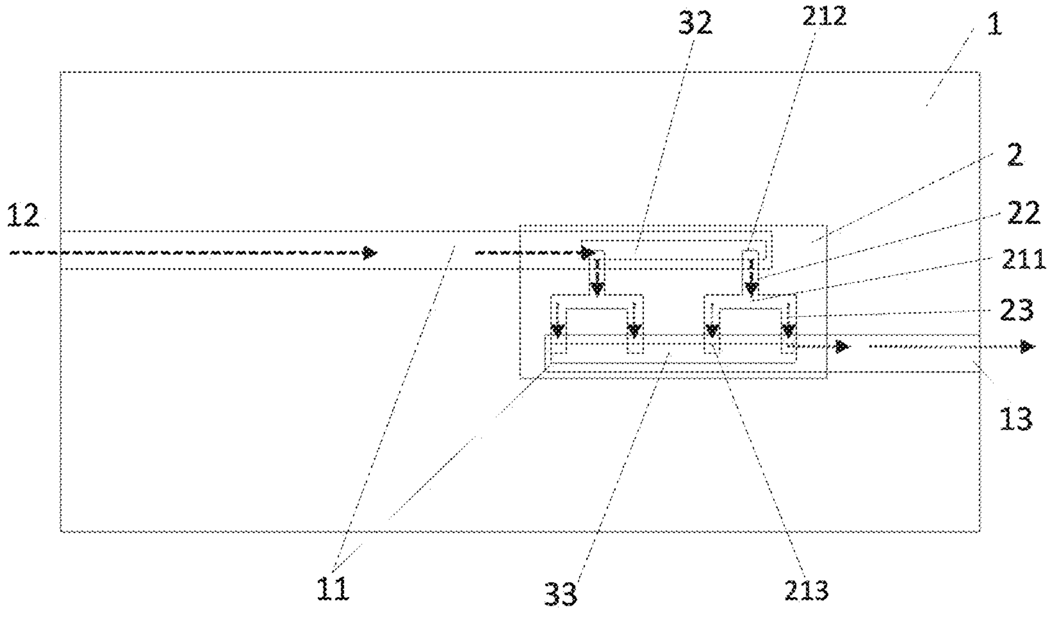
FIG. 6 shows a schematic top-view of the embodiment of the collection device from FIG. 1 with a schematic indication by dashed arrows of a path made by a sample, such as a breath sample from the sample inlet (12) via a first sample guiding conduit (11) made within the base structure (10) to sample inlet opening (32) for entering the impaction channels within the chip (2) where the collection of the particulate matter happens by impaction within the T-junctions (211), after which the reminder of the sample (symbolically represented by a dashed arrow that is thinner than the dashed arrow entering the T-junctions) exists the grooves of the chip (2) through the sample outlet opening (33) and proceeds by the second sample guiding conduit (11) to the sample outlet (13) leading outside of the collection device (1)

An example of how the sample inlet channels (22) can be connected with the sample outlet channels (23) via a T-junction is shown in FIG. 5 as well as in FIG. 6 schematically showing by dashed arrows the path a sample makes after entering into the showed therein embodiment of the disclosed herein collection device via a sample inlet (12) through the T-junctions of the chip, where the collection of the particulate matter takes place by impaction, till the sample outlet (13) leading the remainder of the sample after the impaction to the outside of the collection device.

In a preferred embodiment, the base structure (10) will be made of a rigid material, preferably resistant to being exposed to temperatures typical of thermocycling conditions, e.g. resistant to temperatures of at least 80° C. or 90° C., preferably higher. Advantageously, the collecting device will be disposable and consequently the base structure can be made of a thermoplastic material; for example from polycarbonate, like black (medical grade) polycarbonate. Black, generally dark, or even opaque, and/or generally non-reflective materials have the advantage of reducing reflection when light-based detection is considered, and consequently may be preferred in certain embodiments. In possible embodiments, the chip can be made from silicon, the cover can be made from polymer laminate like PET, polyester with adhesives and/or the base structure can be made in polycarbonate, PMMA, etc.

The base structure will support or enclose the chip that can be e.g. glued thereto or stably positioned therewith thanks to the presence of the cover (3), preferably being a multi-layer cover.

When the base structure (10) is provided in a form of a baseplate, alternatively termed as a test-card, i.e. appearing to have two major planes, the chip (1) may preferably be positioned horizontally with respect to the major planes of such visibly flat base structure.

In an alternative embodiment, the chip can possibly be positioned vertically, which can be achieved by e.g. changing the routing in the base structure (10). Horizontal positioning of the chip (1) with respect to the base structure is however preferred for its compactness, advantages during assembly, as well as final collection device geometry.

Figure 2:
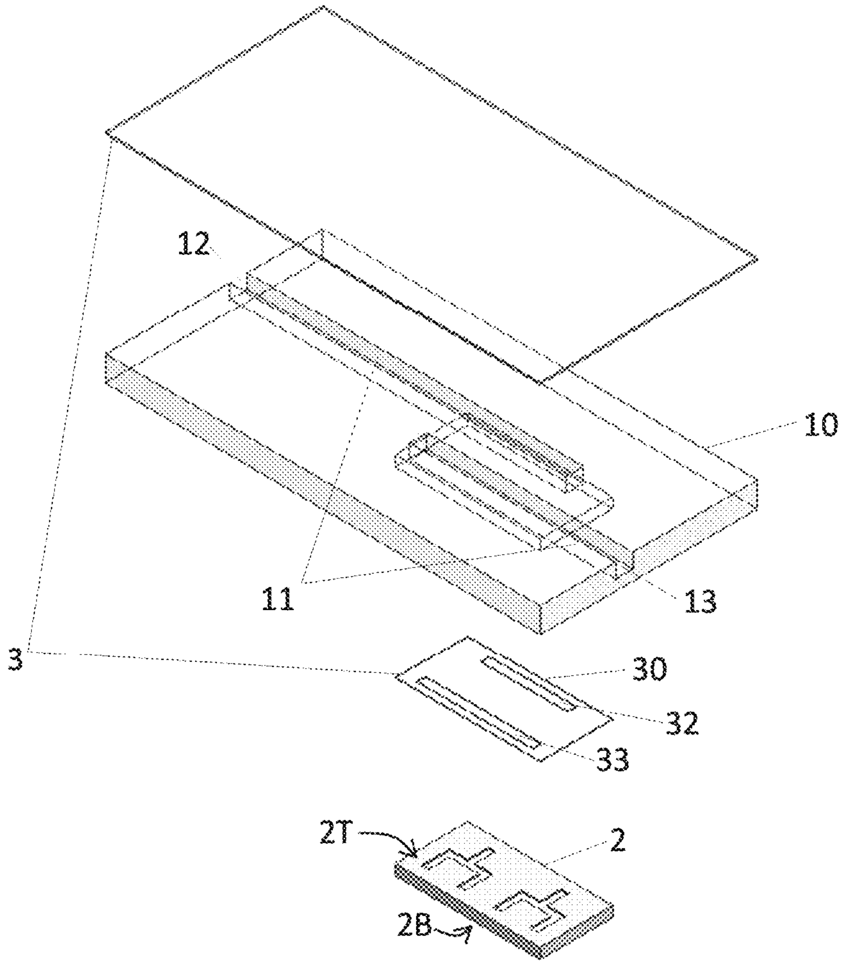
FIG. 2 shows an exploded view of the embodiment of the collection device shown in FIG. 1, which clearly shows two layers of the cover (3), being an outer layer covering the base structure (10) and the chip-contacting layer (30) comprising two openings, one of said openings contacting the first sample guiding conduit (11) extending from the sample inlet (12) and therefore defining together with the structures of the chip the sample inlet opening (32), and the second opening contacting the second sample guiding conduit (11) leading to a sample outlet (13), and therefore defining together with the structures of the chip the sample outlet opening (33). The top (2T) and the bottom (2B) surfaces of the chip are also indicated.
Figure 9:
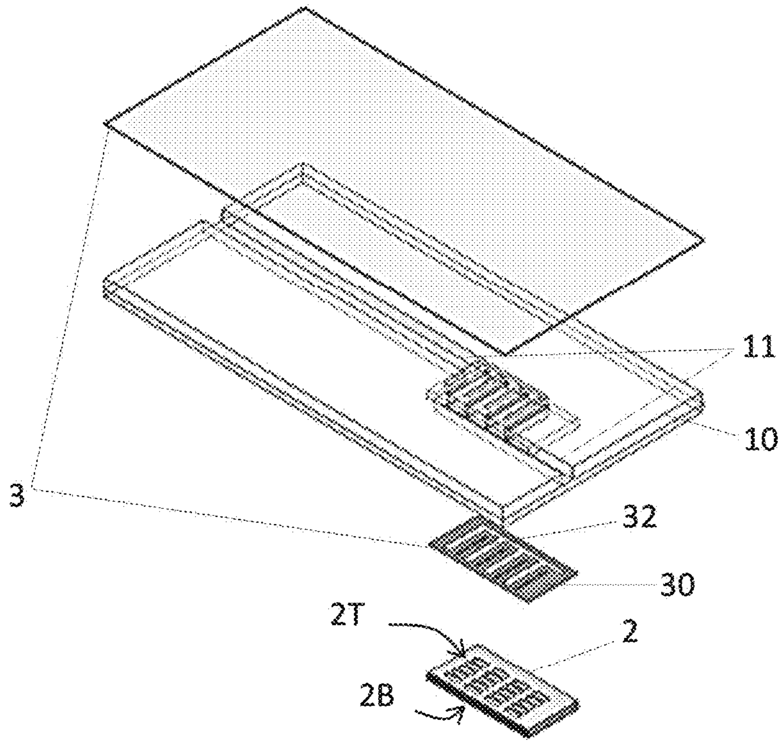
FIG. 9 shows an exploded view of the embodiment of the collection device shown in FIG. 8, which comprises the cover (3) that contains a chip-contacting layer (30) that together with the structures of the chip (2) creates sharp bends for enhancing impaction. The top (2T) and the bottom (2B) surfaces of the chip are indicated.
Figure 10:
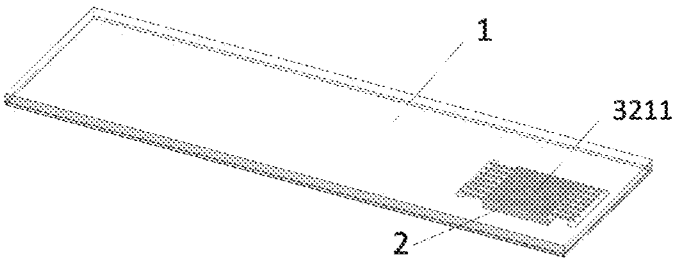
FIG. 10 shows another possible embodiment of the collection device (1) wherein the base structure (10) is made from a transparent rigid material and the cover (3) comprises 3 layers, wherein the chip-contacting layer (30) of the cover comprises a plurality of parallel through-holes that interchangeably define a plurality of parallel sample inlet channels (322) that connect with a sample inlet opening (32) made as a through-hole in another layer of the cover (3), and a plurality of parallel sample outlet channel (323) that connect with a sample outlet opening (33) made a second through-hole the other layer of the cover (3)
Figure 11:
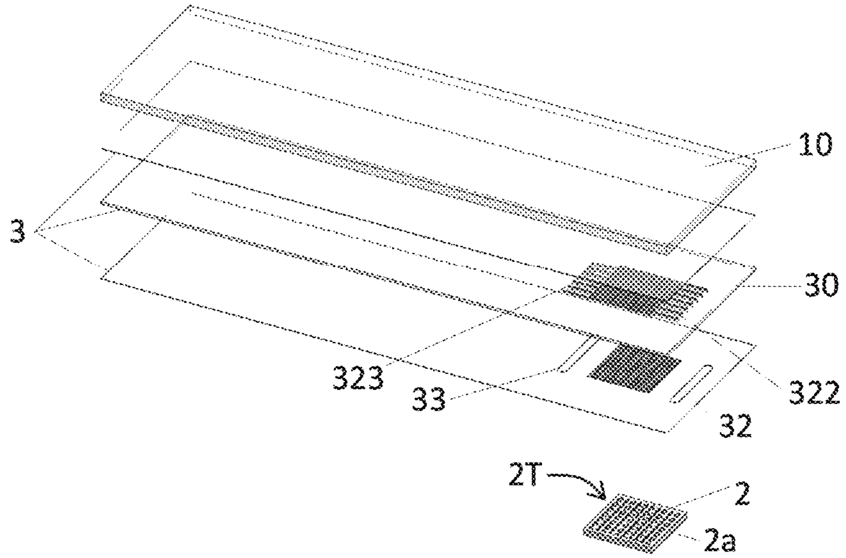
FIG. 11 shows an exploded view of the embodiment of the collection device shown in FIG. 10. In this exploded view, the transparent base structure (10) is positioned on the top of the scheme. Below, the three exemplary layers of the cover (3) are represented, showing distinct structure as manufactured therewith as through holes, for example being the parallel sample inlet and outlet channels (322, 323) in the chip-contacting layer (30), or the through-holes corresponding to the sample inlet opening (32) or the sample outlet opening (33) in the layer underneath the chip-contacting layer (30). On the bottom of the scheme, the chip (2) is shown with an indication of its patterned top surface (2T) and its side exposed to the direction from which the sample is provided into the chip, i.e. the proximal side (2*a*)

Exemplary embodiments of collection devices comprising such substantially flat or card-shaped base structures (1) and chips horizontally positioned therewith are shown as assembled entities in FIGS. 1, 8, 10 and 13, and in exploded view in FIGS. 2, 9, and 11.

Depending on the side from which a sample will be directed into the impaction channels (21) of the chip (2), regardless of the shape (square, rectangular, or even oval or round) of the chip it will be possible to say that the chip (2) is defined by a proximal side (2*a*), i.e. the side from which the sample enters the chip, possibly being the side from which air or breath is blown into the collecting device, and by a distal side (2*b*) opposite to the proximal side (2*a*), i.e. being the side from which the sample, e.g. air, exits the collecting device, and by two lateral sides (2*c*, 2*d*) connecting the proximal side (2*a*) and the distal side (2*b*), in addition to the top surface (2T) and the opposite thereto bottom surface (2B).

Figure 3:
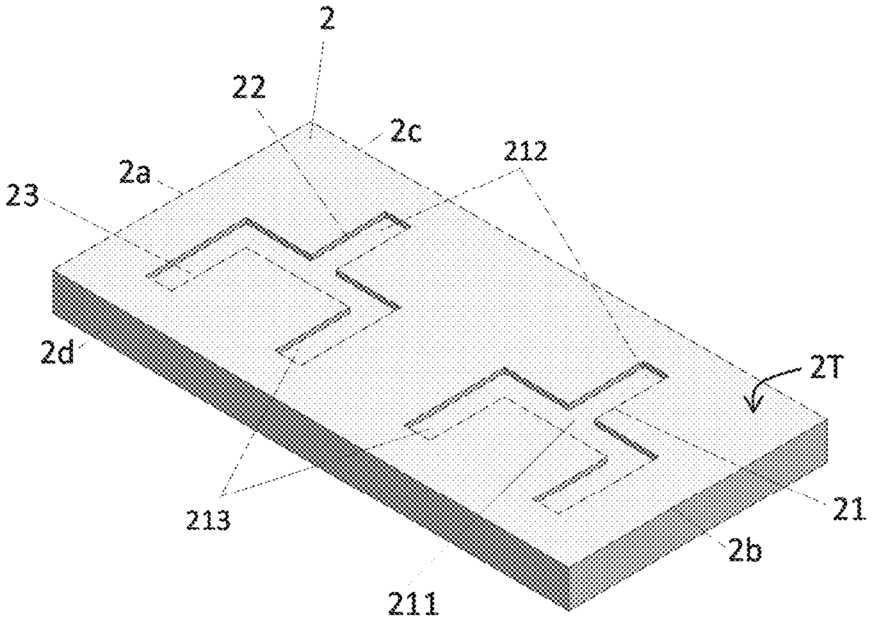
FIG. 3 shows a simplified schematic representation of a chip shown as part of the embodiment of the collection device shown in FIG. 1, the representation of the chip comprising two impaction channels symbolized as two adjacent T-junctions (211) in the top surface (2T) of the chip.
Figure 7:
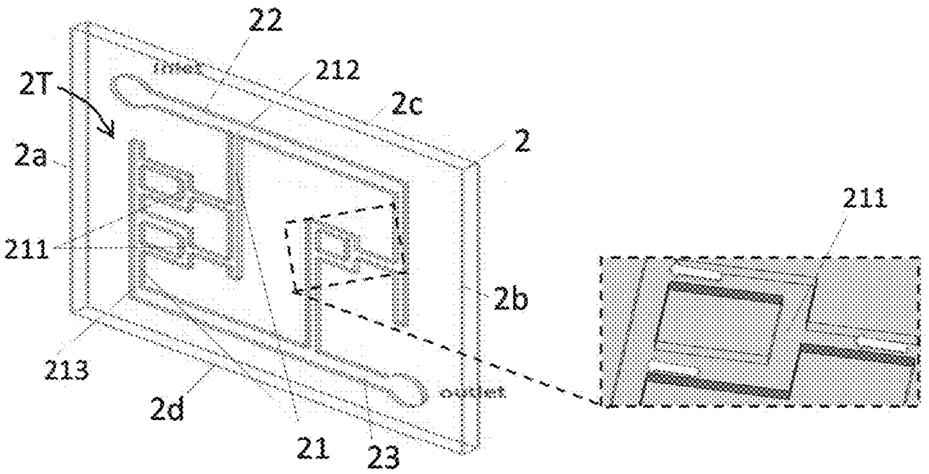
FIG. 7 shows a different schematic and simplified representation of another embodiment of a chip (2) that comprises differently arranged impaction channels (21) and better visible and longer than in the embodiment of FIG. 3 patterned grooves that together with chip-contacting cover define a sample inlet channel (22) and a sample outlet channel (23). On the right-hand-side, a panel shows an enlarged section of the chip containing a T-junction (211) with arrows symbolically indicating the path a sample makes within T-junction while being subject to collection of particulate matter via impaction.
Figure 8:
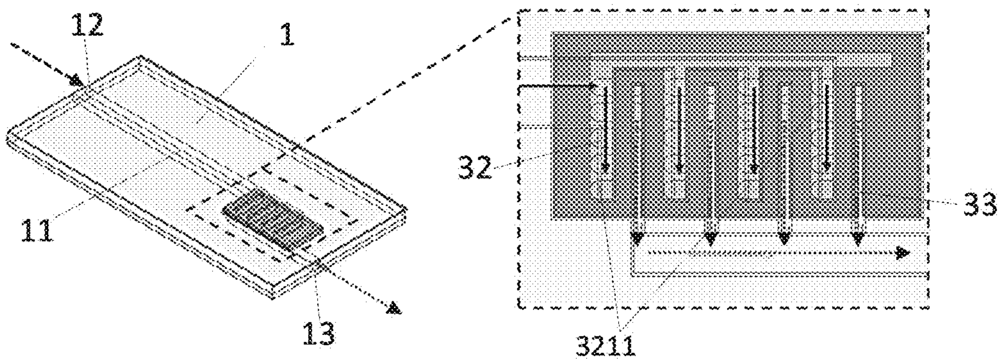
FIG. 8 shows another and a similar to the one of FIG. 1 embodiment of the collection device (1) wherein the base structure (10) also comprises two sample guiding conduits (11), one extending from the sample inlet (12) to the chip (2) and the second one leading therefrom to a sample outlet (13). As in FIG. 6, direction in which a fluid sample enters and exits the collection device is represented by dashed arrows. In this embodiment, the chip-contacting layer (30) of the cover comprises a branched through-hole defining the sample inlet opening (32) and also participates with the chip (2) in creating sharp bends for more efficient impaction. In this embodiment, the sharp bends are created using the cover (3) and the chip (2). The transparent zone (3211) for presenting to light-based detection the contents of the T-junctions with the possibly captured particulate matter is indicated in the enlarged section of the collection device (1) shown in the right-hand-side, together with the schematic indication of the path as made by the sample during the particulate matter collection process.
Figure 12:
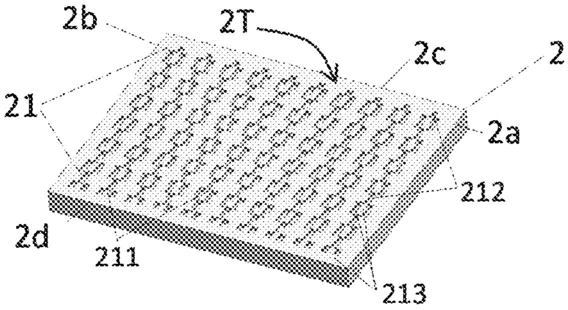
FIG. 12 shows a schematic representation of another embodiment of a chip (2) that is the chip shown in FIGS. 10 and 11 and comprises multiple parallel impaction channels (21), wherein each impaction channel (21) comprises a series of multiple T-junctions (211) that are arranged along the length of each impaction channel (21)

The above explained indication of different sides of possible, though simplified and schematic embodiments of chips for the collecting device as disclosed herein are shown in FIGS. 3, 7, and 12.

In case of such defined sides of the chip, in a possible embodiment, a collecting device can be provided wherein the plurality of the patterned impaction channels (21) the top surface (2T) of the chip (2) are extending between the two lateral sides of the chip (2*c*, 2*d*), and wherein each one of the impaction channels (21) comprising at least one impaction channel inlet (212) are positioned closer to the first lateral side (2*c*) than to the second lateral side (2*d*), and wherein the at least one impaction channel outlet (213) is positioned closer to the second lateral side (2*d*) than to the first lateral side (2*c*).

In a related embodiment, a collecting device can be provided, wherein the cover (3) comprises one or more openings comprising an opening positioned entirely or at least partially (as shown in enlarged panel of FIG. 8) in the proximity of the chip's proximal side (2*a*) for defining the at least one sample inlet opening (32). Analogously, in a further embodiment the collecting device is provided comprising a second opening positioned in the proximity of the chip's distal side (2*b*) for defining the at least one sample outlet opening (33).

As it will be seen from the exemplary embodiments of the collection devices in FIGS. 1, 8, 10 and 13 in view of the indication of sides of chips as indicated in FIGS. 3, 7, and 12, the orientation of the T-junctions (211) is shown as perpendicular to the direction in which a sample, such as air blown by a user, is directed into the chips for collection of the particulate. This orientation of the T-junctions is merely exemplary and other orientations are possible For example, the orientation of the T-junctions can be rotated with respect to how they are shown in said Figures; to do so, the chip-contacting layer (30) may also be rotated. For example, to have the T-junctions rotated 90°, an extra bend or extra bends can be added on e.g. channel 22 or 212 resulting in a similar result as shown in the schematic representation of the chip of FIG. 7.

In particularly preferred from manufacturing-perspective embodiments of the disclosed herein collection devices, the cover (3) will be a multi-layer cover (3) or a composite cover (3) comprising two or more layers. Examples of such layers in possible embodiments of such multi-layer cover (3) can be seen in the exploded view FIGS. 2, 9, and 11. Alternatively, the cover can be manufactured as monobloc that is 3D printed or appropriately moulded. In such case the monobloc constitutes a single layer cover (3) embodiment wherein the chip-contacting layer (30) is the single layer of the monobloc.

Figure 4:
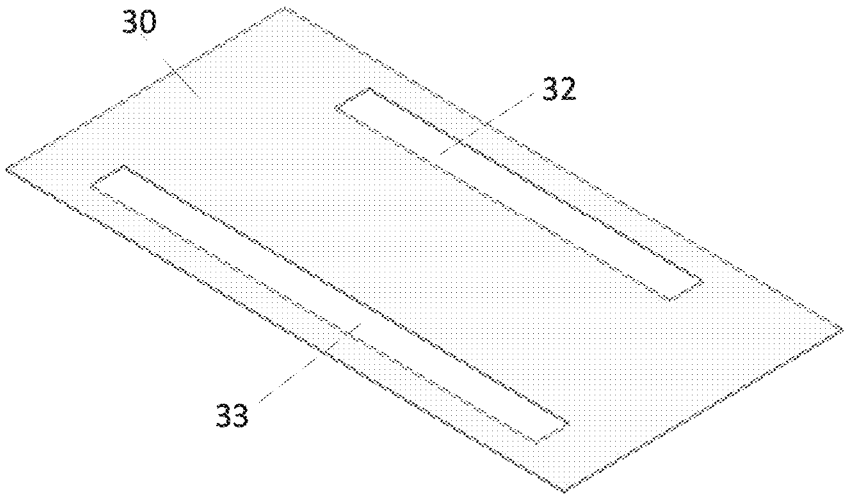
FIG. 4 shows a chip-contacting layer (30) of the cover (3) from the embodiment of the collection device shown in FIG. 1, the chip-contacting layer (3) comprising two openings that when laid on the chip (2) define the sample inlet opening (32) and the sample outlet opening (33)

As already mentioned, in a preferred embodiment, a collecting device (1) is provided wherein at least one of the layers of the cover (3) comprises one or more openings comprising at least a first opening corresponding to the at least one sample inlet opening (32), and possibly further comprises a second opening corresponding to the at least one sample outlet opening (33), possibly wherein the at least one of the layers of the cover (3) is the chip-contacting layer (30) such as the examples of the chip contacting layers seen in in the exploded view FIGS. 2, 9, and 11 as well as in FIG. 4.

In possible advantageous embodiments of the collection device, any one of the cover (3) or the base structure (10) or both can be transparent.

In another embodiment, a collecting device is provided, wherein at least one of the layers of the cover (3) is sticky on at least one side and/or is made from a foil, preferably being a transparent and/or flexible foil. For example, when looking at the exploded view in FIG. 11 the layer of the cover (3) that is the closest to the rigid base structure (10) can be made from a double-sided tape for connecting additional layers and/or parts of a surface of the chip. In such case, the chip-contacting layer (30) can be made of a foil that is not sticky from any side while the final layer containing the sample inlet and outlet openings (32 and 33) can then be made by a foil that is sticky from at least one side. Alternatively, the layer of the cover (3) that is the closest to the rigid base structure (10) can be entirely eliminated in case the chip-contacting layer (30) is made sticky on its side facing the transparent rigid base structure (10). Many alternative arrangement can be envisaged of connecting the layers of the cover (3), which consequently will not be discussed further herein.

Figure 13:
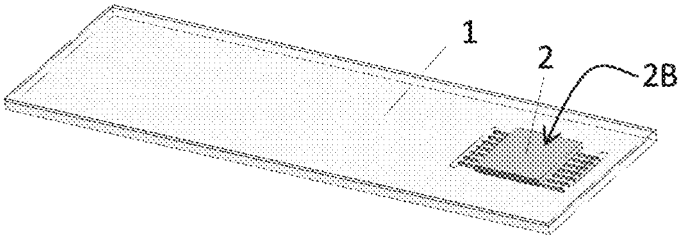
FIG. 13 shows the bottom side of the embodiment of the collection device (1) shown in FIGS. 10 and 11, wherein the bottom side (2B) of the chip (2) that is arranged to contact a heating source like a thermoelectric cooler (TEC)
Figure 14:
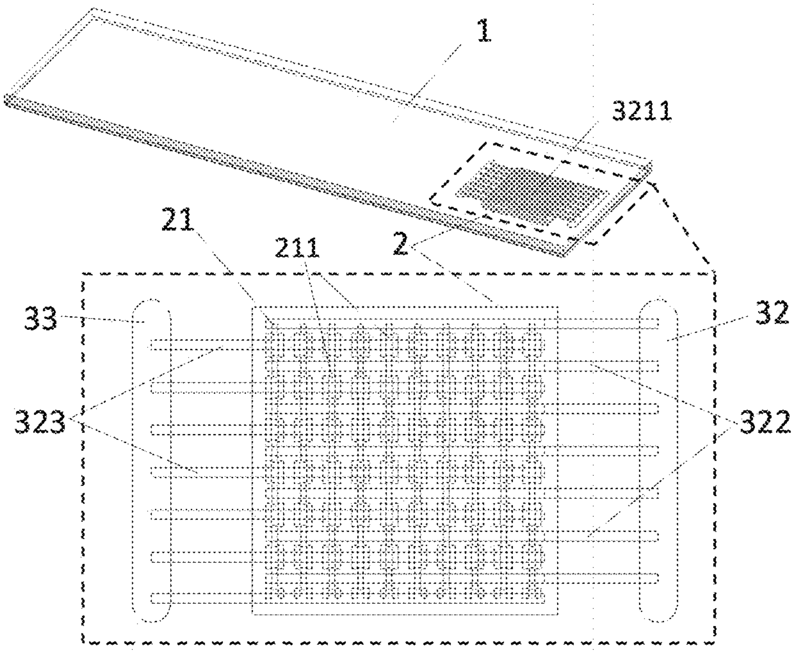
FIG. 14 shows the embodiment of the collection device (1) shown in FIG. 10 and a bottom panel that zooms in on the top-view alignment of the chip (2) and the part of the multi-layer cover (3) comprising the plurality of parallel sample inlet channels (322) that connect with a sample inlet opening (32) and are interchangeably arranged with respect to the plurality of parallel sample outlet channel (323) that connect with a sample outlet opening (33)
Figure 15:
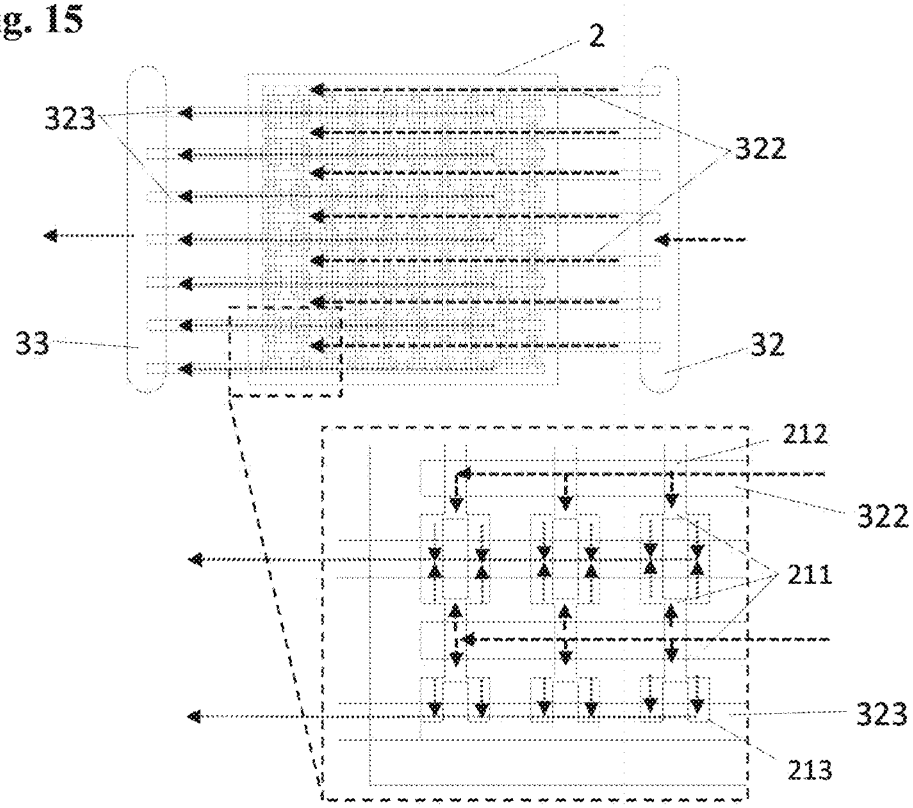
FIG. 15 shows the zoomed-in in FIG. 14 top-view alignment from of the chip (2) with the part of the multi-layer cover (3) comprising the functional through-holes in the appropriate cover layers that define the path along which the sample enters the impaction zone of the chip (2) thus allowing collection of the particulate matter potentially comprising the analyte of interested to be collected and then detected within the grooves patterned on the top surface of the chip (2). The path made by the sample is schematically indicated by dashed arrows. The bottom pane shows a further zoomed-in top-view of a part of the chip (2) and the cover (3) clearly indicating the entry and exit points from the T-junctions (211) where the impaction happens. The entry path is represented by relatively thicker dashed arrows while the exit path is represented by relatively thinner dashed arrows.
Figure 16:
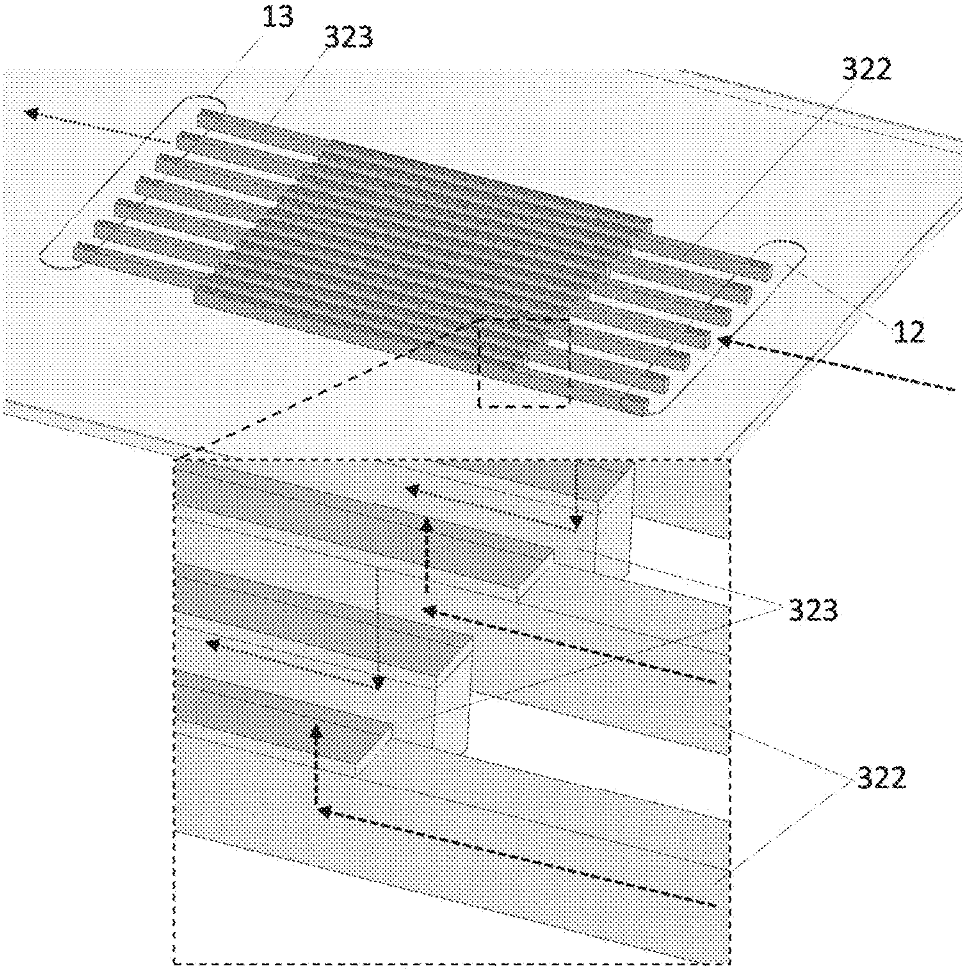
FIG. 16 shows a 3D representation of the parallel sample inlet and outlet channels (322, 323) extending from the sample inlet opening (32) or the sample outlet opening (33), respectively. The bottom panel zooms in on the dead-ends of two sample outlet channels (323) that are positioned between three sample inlet channels (322). The zoomed-in section shows that there is no fluidic communication between the inlet and the outlet channels (322, 323) other than by the impaction zone of the chip (for clarity the chip is not shown but the path the sample makes is indicated by dashed arrows as in FIG. 15)

In another possible embodiment, a collecting device can be provided, wherein at least one of the layers of the cover comprises one or more through-holes that at least partially define any one of the at least one sample inlet channel (322) or the at least one sample outlet channel (323). Examples of such embodiment of the collecting device are shown in FIGS. 10, 11, and 13, with a more detailed schematic views shown in FIGS. 14, 15 and 16 detailing how such created multiple sample inlet channels (322) and multiple sample outlet channels (323) can be arranged and direct samples to and outside an impaction zone created within a chip (to e.g. exemplary impaction channels (21) as shown in a schematic chip example of FIG. 12).

In a further embodiment, a collecting device can be provided wherein the cover (3) and optionally the base structure (10) comprises a further one or more ports for introducing and/or removing liquids such as reagents into and/or from the impaction channels (21). An example of such structure can be an opening within the cover (3) or in the base structure (10), or even a removable part positioned in the vicinity of the chip for pipetting thereto e.g. a PCR mastermix or appropriate buffers.

In a further embodiment, a collecting device can be provided, wherein the base structure (10) further comprises one or more subcompartments for reagents or other liquids, preferably wherein one or more of said subcompartments is formed as a blister or as an ampoule, more preferably wherein at least one of the subcompartments comprises a PCR mastermix.

In another possible embodiment, a collecting device is provided, wherein the base structure (10) further comprises one or more sample guiding conduits (11), such as the ones shown or partially shown in FIGS. 1, 2, 5, 6, 8, and 9, possibly and preferably being guiding conduits, and a sample inlet (12), the sample inlet (12) arranged to be in fluid communication with the at least one sample inlet opening (32), and optionally a sample outlet (13), optionally arranged to be in fluid communication with the at least one sample outlet opening (33).

In a further possible embodiment, a collecting device can be provided further comprising a lid for at least partially covering the base structure (10), possibly wherein the lid forms a part of a wall defining the one or more breath guiding conduits (11), e.g. in case the cover (3) is not involved in this, possibly wherein such additional lid provides an additional protection and covers the area of the chip (2) that comprises the one or more of T-junctions (211) and is transparent at least over said area.

In a particularly preferred embodiment, the disclosed herein collecting devices will be adapted to collecting a sample being a breath sample.

Consequently, in a preferred embodiment, a collecting device is provided wherein the base structure (10) or the lid further comprises or is connectable to a removable mouthpiece or a fitting arrangement for connecting further to the removable mouthpiece, wherein the removable mouthpiece when connected to the base structure (10) is arranged to open from one side into the sample inlet (12).

In case of monitoring of infectious diseases, an advantageous embodiment can be envisaged wherein a collecting device is provided comprising a filter arranged to capture air exiting through the sample outlet (13), preferably wherein it is the base structure (10) that comprises such filter arranged to capture air exiting through the sample outlet (13).

In another possible embodiment, a collecting device can be provided further comprising an external casing for fitting the base structure (10) with the removable mouthpiece and/or the filter and/or for proving firm grasp for the user, preferably comprising handles for proving firm grasp for the user.

In a further advantageous embodiment, a collecting device may be provided comprising sensors or connections for sensors for monitoring during the sample collection process, preferably during breath collection process anyone or more of the following parameters: pressure, temperature, humidity, flow rate e.g. airflow including its speed.

Figure 17:
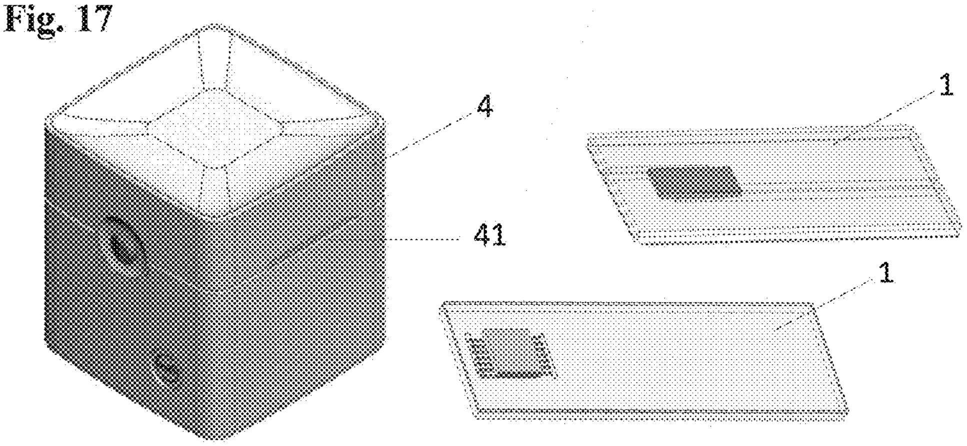
FIG. 17 shows an example of a possible diagnostic system comprising an instrument (4) adapted to accept by an entry slot (41) any one of two exemplary embodiments of the collecting device (1) shown (out of scale due to being enlarged for clarity) on the right-hand-side of the instrument (4) and facing the entry slot (41) with their parts exposing the bottom side of their respective chips. The embodiment of the instrument (4) comprises a heating module for contacting the exposed closed bottom parts of the chips in order to execute a thermocycling programme within their grooves; and further comprise an optic reader for detecting e.g. light signals originating from the structures on top surface of the chip (facing bottom in this schematic representation).

In a yet another embodiment, a collecting device can be provided, wherein the base structure (10) comprises an through-hole (14) for exposing the bottom surface (2B) of the chip (2) for allowing direct contacting of said bottom surface (2B) with the heating source such as a TEC, for example a TEC integrated inside of a an instrument such as the one shown in FIG. 17 for engaging and automated processing of possible embodiments of the disclosed herein collection devices.

In a further embodiment, a collecting device can be provided wherein the transparent zone (3211) of the cover (3), and optionally the lid (30) is protected by a removable element for protecting said transparent zone from dirt, for example a sticker or a liner.

In a practical embodiment, a collecting device can be provided formed as or comprised as part of a card, such as a test card.

In another practical embodiment, a collecting device can be provided further comprising a code such as a barcode, preferably provided on the base structure (10) or on the lid.

In a related aspect, the present disclosure also provides a breath analyser comprising the collecting device (1) as described above, and a mouthpiece wherein the cross-section of the part of the mouthpiece designed to engage with the user's lips is defined by two wider rims and two perpendicular thereto shorter rims defining the positioning of the mouthpiece with respect to the lips of the user, wherein the collecting device (1) is positioned such that the chip (2) is positioned horizontally with respect to the wider rims of the mouthpiece such that the chip (2) is positioned horizontally with respect to the ground level and/or to the base structure and to the flow of air that the user exhales into the card/collecting device via the mouthpiece.

To the knowledge of the inventors, no devices using such practical horizontal incorporation of the chip in collecting device are known, which geometrically advantageous arrangement has the benefit of allowing the collected particles to be readily detected directly using at least a part of the collecting device with the chip upon provision to an appropriate analysis system.

The breath analysers as discussed herein can be manufactured as many possible embodiments, including, just to name a few, addition of practical casings and/or arrangements making the embodiments connectable to disposable, standard and/or adjustable mouthpieces (e.g. smaller ones for children); including further mechanical additions such as handles for firm grasp by children or e.g. elderly; adjustment means to ensure steady airflow and comfort of breathing during sample collection; arrangements for connecting with filter such as standard filters; sensors; connection means to a device comprising a screen either via cable connection or wirelessly to e.g, a smartphone, possibly with a provision of an interface like an app for visualising airflow or monitoring if enough sample is being acquired during the collection process etc.

In a yet another aspect, a diagnostic system is further provided herein comprising the collecting device (1) of the disclosure, wherein the system further comprises a heating module and a reader, wherein the system is engageable with the collecting device and adapted to perform thermocycling on and reading output signals from the chip (2) directly.

In a preferred embodiment, such diagnostic system can be provided wherein the heating module and the reader form one integrated subsystem of the diagnostic system, such as in the form of an instrument as shown in FIG. 17.

Last but not least, provided herein are also uses of the collecting device or the system of the disclosure, for testing a human subject for a presence of a metabolic condition or a disease, the disease preferably being an infectious disease caused by an infectious agent, even more preferably being an infectious disease caused by an infectious agent that undergoes shedding into material exhaled by a user, most preferably being a virus such as SARS-CoV-2 virus.

What is claimed is:

1. A collecting device for sampling particulate matter from a sample, the collecting device comprising:

a base structure;

a monolithic silicon chip supported by said base structure, the chip comprising at least two opposite sides and a top surface and an opposite thereto bottom surface, wherein the bottom surface is closed allowing contacting with a heating source and wherein the top surface comprises a plurality of patterned impaction channels for capturing particulate matter present in the sample, and extending between the at least two opposite sides of the chip, each one of the impaction channels comprising at least one impaction channel inlet and at least one impaction channel outlet and comprising one or more T-junctions between the at least one impaction channel inlet and the at least one impaction channel outlet;

a cover in contact with the base structure and comprising a chip-contacting layer that is in contact with the chip's top surface and is at least partially covering the impaction channels, wherein the cover is configured to define at least one sample inlet opening and at least one sample outlet opening, and further together with the chip's top surface to define an at least one sample inlet channel that is in fluidic connection with the at least one impaction channel inlet and that is arranged for guiding at least a part of the sample into the one or more T-junctions, and an at least one sample outlet channel that is in fluidic connection with the at least one impaction channel outlet and that is positioned downstream of the one or more T-junctions, wherein the cover is arranged such that fluidic connection between the at least one sample inlet channel and the at least one sample outlet channel is established by the one or more T-junctions; and a transparent zone that covers an area of the top surface of the chip, which area comprises the one or more of T-junctions for presenting said area to light-based detection of an analyte possibly captured in said one or more of T-junctions.

2. The collecting device according to claim 1, wherein at least one of the layers of the cover comprises one or more openings comprising at least a first opening corresponding to the at least one sample inlet opening.

3. The collecting device according to claim 2, wherein the one or more openings further comprises a second opening corresponding to the at least one sample outlet opening.

4. The collecting device according to claim 2, wherein the at least one of the layers of the cover is the chip-contacting layer.

5. The collecting device according to claim 1, wherein at least one of the layers of the cover is sticky on at least one side and/or is made from a foil.

6. The collecting device according to claim 5, wherein the foil is a transparent and/or flexible foil.

7. The collecting device according to claim 5, wherein at least one of said layers comprises one or more through-holes that at least partially defines any one of the at least one sample inlet channel or the at least one sample outlet channel.

8. The collecting device according to claim 1, wherein the cover comprises a further one or more ports for introducing and/or removing liquids into and/or from the impaction channels.

9. The collecting device according to claim 1, wherein the cover and the base structure comprise a further one or more ports for introducing and/or removing liquids into and/or from the impaction channels.

10. The collecting device according to claim 1, wherein the base structure further comprises one or more subcompartments for reagents or other liquids.

11. The collecting device according to claim 10, wherein one or more of said subcompartments is formed as a blister or as an ampoule.

12. The collecting device according to claim 10, wherein at least one of the subcompartments comprises a PCR mastermix.

13. The collecting device according to claim 1, wherein the base structure further comprises one or more sample guiding conduits, and a sample inlet, the sample inlet arranged to be in fluid communication with the at least one sample inlet opening.

14. The collecting device according to claim 13, wherein a sample outlet is arranged to be in fluid communication with the at least one sample outlet opening.

15. The collecting device according to claim 13, the collecting device further comprising a lid for at least partially covering the base structure.

16. The collecting device according to claim 15, wherein the lid forms a part of a wall defining one or more breath guiding conduits.

17. The collecting device according to claim 15, wherein the lid covers the area of the chip that comprises the one or more of T-junctions and is transparent at least over said area.

18. The collecting device according to claim 13, wherein the base structure further comprises or is connectable to a removable mouthpiece or a fitting arrangement for connecting further to the removable mouthpiece, wherein the removable mouthpiece forms a connection with the sample inlet to allow the sample to enter the collection device.

19. The collecting device according to claim 15, wherein the lid further comprises or is connectable to a removable mouthpiece or a fitting arrangement for connecting further to the removable mouthpiece, wherein the removable mouthpiece forms a connection with the sample inlet to allow the sample to enter the collection device.

20. The collecting device according to claim 13, wherein the base structure further comprises a filter arranged to capture air exiting through the sample outlet.

21. The collecting device according to claim 13, further comprising an external casing for fitting the base structure with a removable mouthpiece and/or a filter arranged to capture air exiting through the sample outlet and/or for providing firm grasp for the user.

22. The collecting device according to claim 21, wherein the external casing comprises handles for providing firm grasp for the user.

23. The collecting device according to claim 1, further comprising sensors or connections for sensors for monitoring during a sample collection process.

24. The collecting device according to claim 23, wherein the sample collection process is a breath collection process for collection of any one or more of the following parameters: pressure, temperature, humidity, and flow rate.

25. A breath analyser comprising the collecting device according to claim 1, and a mouthpiece, the mouthpiece comprising a user-engaging portion having a cross-section defined by two wider rims and two shorter rims perpendicular thereto wherein the mouthpiece and the collecting device are arranged such that when a user exhales into the mouthpiece, a major plane of the chip is oriented substantially horizontally with respect to a ground level.

26. A diagnostic system comprising the collecting device according to claim 1, wherein the system further comprises a heating module and a reader, wherein the system is engageable with the collecting device and adapted to perform thermocycling on and reading output signals from the chip directly.

27. A method for testing a user for a presence of a metabolic condition or a disease, the method comprising:

providing a sample from the user; and applying the sample to the sample inlet opening of the collecting device according to claim 1, wherein the disease is an infectious disease caused by an infectious agent, or an infectious disease caused by an infectious agent that undergoes shedding into material exhaled by a user, or a virus such as SARS-COV-2 virus.

28. A method for testing a user for a presence of a metabolic condition or a disease, the method comprising:

providing a sample from the user; and applying the sample to the sample inlet opening of the diagnostic system according to claim 26, wherein the disease is an infectious disease caused by an infectious agent, or an infectious disease caused by an infectious agent that undergoes shedding into material exhaled by a user, or a virus such as SARS-COV-2 virus.

* * * * *